United States Patent [19]
Flanagan

[11] Patent Number: 5,171,215
[45] Date of Patent: Dec. 15, 1992

[54] ENDERMIC METHOD AND APPARATUS

[76] Inventor: Dennis F. Flanagan, 1671 W. Main St., Willimantic, Conn. 06226

[21] Appl. No.: 748,555

[22] Filed: Aug. 22, 1991

[51] Int. Cl.⁵ .......................................... A61M 37/00
[52] U.S. Cl. ...................................... 604/22; 604/20; 604/23; 604/289; 604/290; 606/1
[58] Field of Search ................ 128/2, 24 AA, 419 F, 128/798; 604/20, 22, 23, 24, 289, 290, 304, 310, 313, 315, 891.1, 892.1; 606/1

[56] References Cited

U.S. PATENT DOCUMENTS

| | | | |
|---|---|---|---|
| 1,585,104 | 5/1926 | Montgomery | 604/20 |
| 3,474,777 | 10/1969 | Figge et al. | 128/2 |
| 3,561,444 | 2/1971 | Boucher . | |
| 4,127,125 | 11/1978 | Takemoto et al. . | |
| 4,309,989 | 1/1982 | Fahim . | |
| 4,372,296 | 2/1983 | Fahim . | |
| 4,530,360 | 7/1985 | Duarte . | |
| 4,640,689 | 2/1987 | Sibalis | 128/798 |
| 4,657,543 | 4/1987 | Langer et al. | 604/891 |
| 4,722,726 | 2/1988 | Sanderson et al. | 604/20 |
| 4,734,090 | 3/1988 | Sibalis | 128/798 |
| 4,767,402 | 8/1988 | Kost et al. | 604/22 |
| 4,780,212 | 10/1988 | Kost et al. . | |
| 4,787,888 | 11/1988 | Fox | 604/20 |
| 4,808,152 | 2/1989 | Sibalis | 128/798 |
| 4,821,740 | 4/1989 | Tachibana et al. | 128/798 |
| 4,886,514 | 12/1989 | Maget | 604/20 |
| 4,931,046 | 6/1990 | Newman | 604/20 |
| 4,942,883 | 7/1990 | Newman | 128/798 |
| 4,948,587 | 8/1990 | Kost et al. . | |
| 4,953,565 | 9/1990 | Tachibana et al. . | |
| 4,979,938 | 12/1990 | Stephen et al. | 604/20 |
| 5,007,438 | 4/1991 | Tachibana et al. | 128/798 |
| 5,032,109 | 7/1991 | Sibalis | 128/798 |

Primary Examiner—Stephen C. Pellegrino
Assistant Examiner—Glenn Dawson
Attorney, Agent, or Firm—Ira S. Dorman

[57] ABSTRACT

Transfer of substances through the skin at a treatment site is promoted by the combined effects of ultrasonic energy and positive and negative pressure. A device having a cup-shaped body is pressed against the skin; the treating substance is supplied to an interior chamber of the body, and is subjected to pressure and ultrasonic vibrational energy therewithin, while a vacuum is drawn thereabout through a surrounding annular chamber.

19 Claims, 1 Drawing Sheet

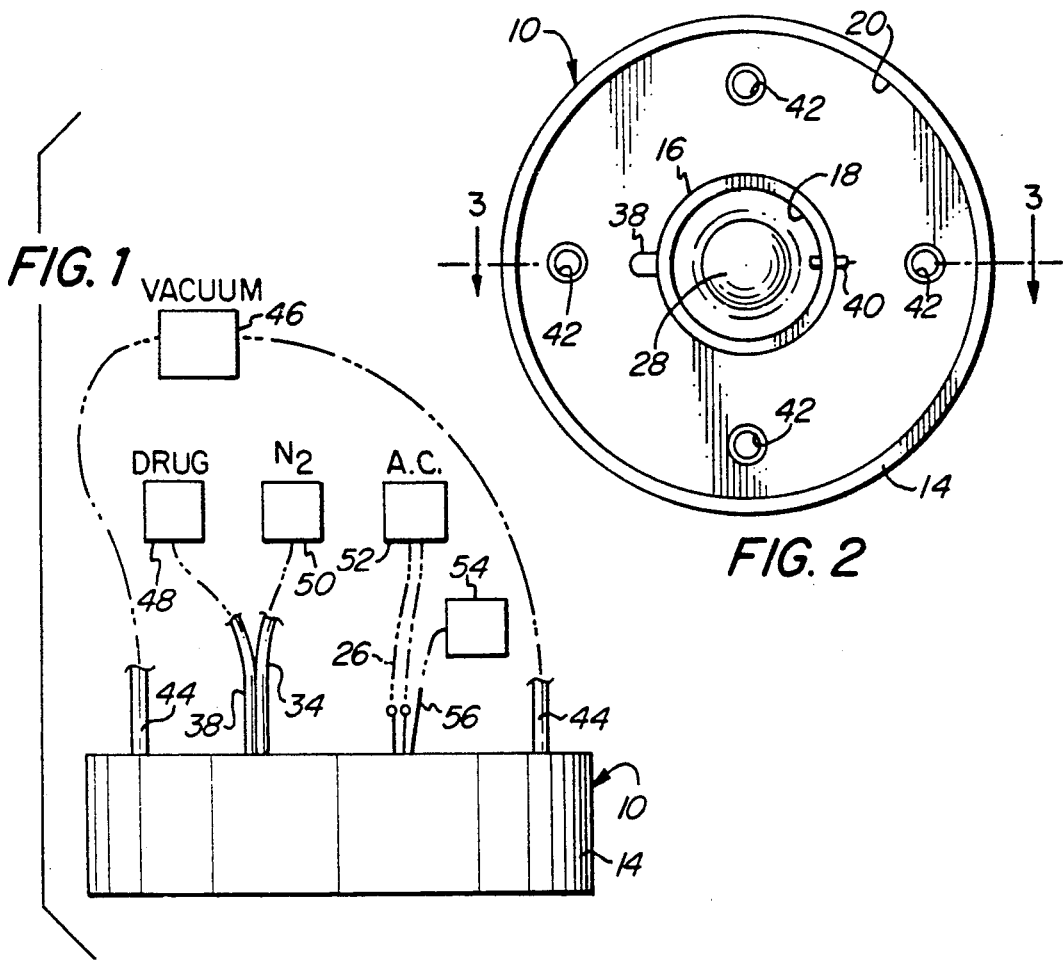
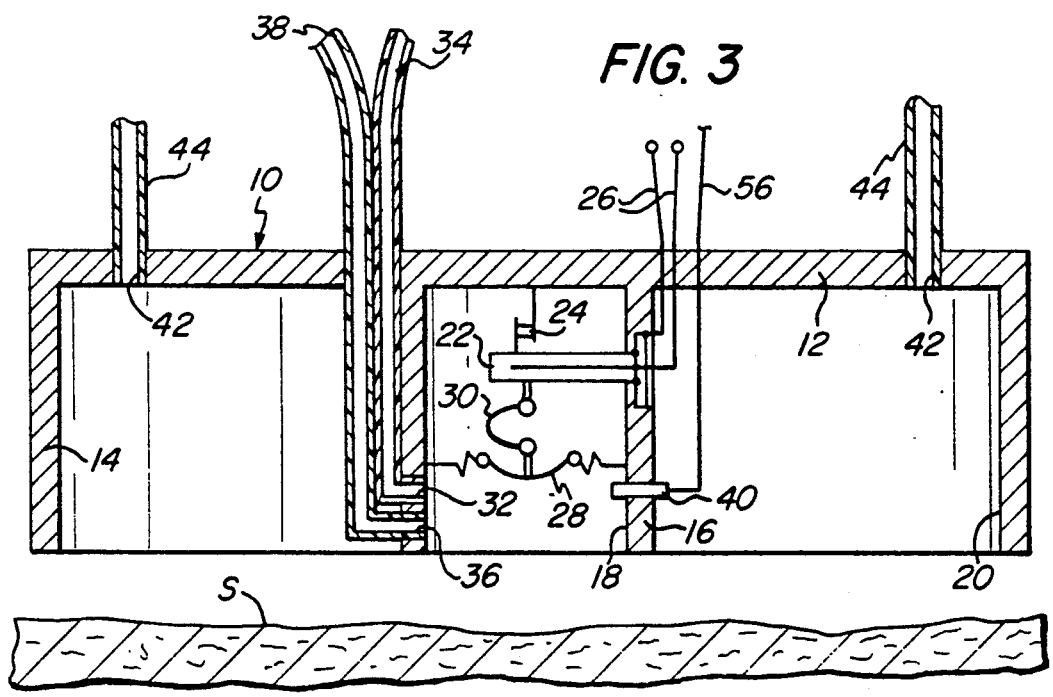

ENDERMIC METHOD AND APPARATUS

BACKGROUND OF THE INVENTION

It is well known in the art to employ ultrasonic energy for effecting and enhancing the delivery of medicaments, applied either topically or furnished from a body implant. The following U.S. patents teach the use of various ultrasound techniques for such purposes: Fahim U.S. Pat. Nos. 4,309,989 and 4,372,296, issued Jan. 12, 1982 and Feb. 8, 1983, respectively; Langer et al U.S. Pat. No. 4,657,543, issued Apr. 14, 1987; Kost et al U.S. Pat. Nos. 4,767,402, 4,780,212 and 4,948,587, issued Aug. 30, 1988, Oct. 25, 1988 and Aug. 14, 1990, respectively; Fox U.S. Pat. No. 4,787,888, issued Nov. 29, 1988; and Tachibana et al U.S. Pat. Nos. 4,821,740 and 4,953,565, issued Apr. 18, 1989 and Sep. 4, 1990, respectively.

The following patents may also be of interest to the subject matter: Boucher U.S. Pat. No. 3,561,444, issued Feb. 9, 1971, teaches an ultrasonic drug nebulizer; Takemoto et al disclose devices for transmitting ultrasonic waves to teeth, in U.S. Pat. No. 4,127,125, issued Nov. 28, 1978; and Duarte describes, in U.S. Pat. No. 4,530,360, issued Jul. 23, 1985, a method for healing bone fractures with ultrasound. Figge et al U.S. Pat. No. 3,474,777, issued Oct. 28, 1969, provides a method for administering therapeutic agents in which a magnetic field is applied to the organism, and iontophoretic drug delivery methods are described in Sanderson et al U.S. Pat. No. 4,722,726, issued Feb. 2, 1988, Newman U.S. Pat. No. 4,931,046, issued Jun. 5, 1990, and Stephen et al U.S. Pat. No. 4,979,938, issued Dec. 25, 1990.

Despite the activity in the art indicated by the foregoing, it would of course be highly advantageous to increase the efficiency by which a substance, especially a medicament, can be transferred through a membranous layer at a treatment site. Accordingly, it is the broad object of the present invention to provide a novel device, system, and method by which such increased efficiency can be realized.

More specific objects of the invention are to provide a device, system and method having the foregoing features and advantages, by which the treating substance may be delivered directly to the site, and which are in addition incomplex, convenient to use, and economical to produce.

SUMMARY OF THE INVENTION

It has now been found that certain of the foregoing and related objects of the invention are attained by the provision of a device that comprises a body defining first and second, directly adjacent lateral chambers, isolated from one another but having open ends disposed on a substantially common plane. The device also includes means for producing ultrasonic vibrational energy within a zone defined at the outer end of the first chamber of its body, means for positively pressurizing that zone, and means for effecting evacuation of the adjacent, second body chamber.

The device will usually also have means for introducing a substance into the outer zone of the first chamber, and it may additionally include means for sensing the temperature therewithin. The second chamber will preferably surround the first, and the two chambers will desirably be separated from one another by a common wall of circular cross section. In a specific embodiment, the body will be of cup-like configuration, and will comprise an inner end wall and a peripheral sidewall, the latter defining the outermost bounds of the second chamber. Ultrasonic energy may be produced with a flexible diaphragm that spans the first chamber of the body and that segregates its outer zone from an inner one, using vibration-generating means that is disposed within the inner zone and is operatively connected to the diaphragm.

Other objects of the invention are attained by the provision of a substance transfer-promoting system that utilizes a device having the features and advantages herein described. The system will additionally include electric power supply means, operatively connected to the vibrational energy-producing means of the device, fluid source means for pressurizing the device, and vacuum-creating means for evacuating the second chamber. It may also comprise substance-source means, operatively connected to the means for introducing, and means for generating, and for responding to, an electrical signal that is indicative of the sensed temperature.

Additional objects of the invention are attained by the provision of a method for promoting endermic transfer, in accordance with which the device described is pressed against the treatment site, with the body so oriented that the membranous layer present thereat overlies and closes its chambers. A treating substance is applied to the site, and while the site is subjected to ultrasonic vibrational energy the first and second chambers of the body are subjected, respectively, to positive and negative pressure. The treatment substance will usually be a liquid medicament, and a gaseous substance will normally be employed for pressurization.

BRIEF DESCRIPTION OF THE DRAWINGS

FIG. 1 is a diagrammatic representation of a system embodying the present invention;

FIG. 2 is a diagrammatic bottom view of a device embodying the invention, utilized in the system of FIG. 1; and FIG. 3 is a sectional view of the device of FIG. 2, taken substantially line along 3—3 thereof and drawn to an enlarged scale.

DETAILED DESCRIPTION OF THE ILLUSTRATED EMBODIMENTS

Turning now in detail to the appended drawing, therein illustrated is a device for use in the delivery of a substance to a site, and for promoting transfer of the substance across a membraneous layer thereat, which device comprises a cup-like body of circular cross section, generally designated by the numeral 10. The body 10 has an end wall 12, from which extend concentrically a circumferential, cylindrical sidewall 14 and a cylindrical interior wall 16; typically, the sidewall 14 will have a diameter of 38 millimeters, and the interior wall 16 will have a diameter of 8 millimeters. The interior wall 16 defines a central chamber 18 and, in cooperation with the sidewall 14, a surrounding annular chamber 20.

A piezoelectric element 22 is mounted on the wall 16 adjacent the inner end of the central chamber 18, and is supported in part by appropriate connecting structure 24; the piezoelectric element 22 is adapted to vibrate at ultrasonic frequencies when supplied with electrical power, for which purposes leads 26 are provided. A flexible diaphragm 28 is disposed across the chamber 18, at a point intermediate its inner and outer ends, and is operatively connected to the piezoelectric element 22 through a spring 30.

Inlet port 32 opens within a zone outwardly of the diaphragm 28 near the mouth of the chamber 18, and is connected to a tube 34 that extends through the end wall 12 of the body 10; a second inlet port 36, having an associated tube 38, opens adjacent the first. Four small apertures 42 are formed through the end wall 12; they open into the annular chamber 20, and each receives a tube 44 (only two of which are visible in FIG. 3). A thermocouple element 40 is mounted through the interior wall 18, to sense the temperature within the central chamber 18.

As seen in FIG. 1, tubes 44 are connected to a vacuum source 46; tubes 34 and 38 are similarly connected, respectively, to a source 50 of nitrogen gas under pressure, and to a drug supply vessel 48. The piezoelectric element 22 is connected to an A.C. power supply 52, through the leads 26, and the thermocouple element 40 is connected, by line 56, to a temperature read-out unit 54.

The device is used by placing its body 10 firmly against the surface of the skin "S," with the open ends of chambers 18, 20 in contact with the skin surface and closed thereby; suction created by actuation of the vacuum source 46 may be relied upon to maintain the body 10 in place, or it can be held manually or mechanically. Perhaps it should be mentioned here that the edges of the walls 14, 16 may be configured to match the contour of any given site, if so desired; they may alternatively or in addition be made of a conformable material, and/or they may cooperate with an applied moldable material for the same purpose. These features are considered to be encompassed by reference herein to the "substantially common plane" on which the adjacent chambers open.

Actuation of the drug supply 48 and the nitrogen gas supply 50 (e.g., by opening of valves, not shown, in the tubes 34, 38) will cause the treating substance to be delivered under pressure to a zone of the central chamber 18 lying outwardly of the diaphragm 28; actuation of the power supply 52, and consequential vibration of the piezoelectric element 22 and the diaphragm 28, will subject the site to ultrasonic frequency energy. The combined effects of the pressure applied, the ultrasonic energy, and the maintained vacuum will cause the delivered substance to permeate the skin in a highly effective and efficient manner.

As noted above, it is well known that ultrasonic vibrational energy can produce a substantial increase in the rate of endermic transport of a substance. In accordance with the present invention, however, that effect is supplemented by not only the force of the positive pressure that is developed within the inner chamber 18 of the device, which serves to stretch the skin and thereby to increase the exposed surface area and to open pores, glands and follicles, but also by the vacuum that is applied through the surrounding annular chamber 20. Vacuumization is believed to generate a sub-epithelial force which draws the applied substance into the skin; but regardless of theory, the effect is found to substantially enhance the infusion rate.

Thermocouple element 40 serves simply to indicate if the amount of heat generated at the treatment site has become excessive. Actual temperatures may be registered by the readout unit 54, which may in addition, or alternatively, incorporate or be connected to a visible or audible alarm. Although not illustrated, it will be appreciated that the system and device of the invention may also include pressure sensing means, preferably as a component of a feedback system by which pressure within the interior chamber 18 can be monitored and controlled, so as to maintain it at an optimal level of, for example, 10 to 80 lb/in$^2$. It will also be appreciated that a factor to be considered in this regard is the achievement of a suitable balance with the vacuum effect, which will typically be drawn at a level of 10 to 80, and preferably about 30, lb/in$^2$.

The ultrasonic generator will usually be operated at a frequency between 20 kilohertz to 10 megahertz, and at an intensity ranging from one to four wats/cm$^2$; exposure time will normally be 30 seconds to 15 minutes. The conditions of treatment may however vary widely, and will depend upon a number of factors, including the molecular and cellular structure of the membranous surface being treated, the nature of the substance being delivered for transmission therethrough, the degree of permeation that is to be achieved, etc. Different modes of ultrasonic energy exposure may be used (e.g., pulsed or continuous), and phasing of the several functions may vary, albeit that pressurization, evacuation and ultrasonic exposure must occur simultaneously during at least a portion of any given treatment cycle.

The substance applied to the site may be virtually any biologically active drug or medicament that can effectively be used in an endermic method, irrespective of form (e.g., an aqueous solution or a gel) and composition. An especially notable embodiment of the method is however one in which a local anesthesia is administered, as preliminary to dental work, obviating any need for mechanical puncturing of the skin. It should be appreciated, moreover, that the invention is not limited to the delivery and transport of medicaments to and through animal tissues and membranes; other applications may occur to those skilled in the art, and are deemed to fall within the scope of the present concept.

Thus, it can be seen that the present invention provides a novel device, system, and method for increasing the efficiency of delivery and transfer of a substance, especially a medicament, to and through a membranous site. The device, system and method are incomplex, convenient to use, and economical to produce, and are nevertheless highly effective in achieving their intended purposes.

Having thus described the invention, what is claimed is:

1. A device for promoting the transfer of a substance through a membranous layer at a treatment site, said device comprising:

a body having wall structure defining first and second, directly adjacent lateral chambers, said chambers having open outer ends disposed on a substantially common plane and being otherwise isolated from one another;

means operatively connected to said body for producing ultrasonic vibrational energy within an outer zone at said outer end of said first chamber;

means communicating with said first chamber for positively pressurizing said outer zone of said first chamber; and means communicating with said second chamber for effecting evacuation of said second chamber;

whereby the combined effects of the pressure applied, the ultrasonic energy and the maintained vacuum serve to promote the transfer of said substance through the membranous layer at the treatment site 2. The device of claim 1 wherein said device additionally includes means communicating with said first chamber for introducing a substance into said outer zone of said first chamber.

3. The device of claim 2 wherein said means for producing comprises a flexible diaphragm spanning said first chamber and segregating said outer zone from an inner zone thereof, and means for generating vibrational forces at ultrasonic frequencies, said means for generating being operatively connected to said diaphragm and being disposed within said inner zone of said first chamber.

4. The device of claim 2 wherein said means for pressurizing comprises a first passage constructed and configured for the flow of a gaseous substance under positive pressure; and wherein said means for introducing comprises a second passage constructed and configured for the flow of a liquid substance.

5. The device of claim 1 wherein said second chamber surrounds said first chamber.

6. The device of claim 5 wherein said first and second chambers are separated from one another by a common interior wall.

7. The device of claim 6 wherein said body is of cuplike configuration and includes an inner end wall from which said interior wall extends, and an exterior sidewall that extends from about the periphery of said end wall, said sidewall defining the laterally outer bounds of said second chamber.

8. The device of claim 1 additionally including means for sensing the temperature within said outer zone.

9. A system for promoting transfer of a substance through a membranous layer at a treatment site, said system comprising:
(a) a device comprising a body having wall structure defining first and second, directly adjacent lateral chambers, said chambers having open outer ends disposed on a substantially common plane and being otherwise isolated from one another; electrically powered means, operatively connected to said body, for producing, within an outer zone defined at said outer end of said first chamber, ultrasonic vibrational energy; means communicating with said first chamber for positively pressurizing said outer zone of said first chamber; and means communicating with said second chamber for effecting evacuation of said second chamber;
(b) electric power supply means operatively connected to said means for producing, for generating said energy;
(c) fluid source means for supplying fluid under positive pressure, operatively connected to said means for pressurizing; and
(d) vacuum-creating means operatively connected to said means for effecting evacuation.

10. The system of claim 9 wherein said means for pressurizing comprises a first passage constructed and configured for the flow of a gaseous substance, and wherein said device additionally includes means communicating with said first chamber means for introducing a substance into said outer zone thereof, said means for introducing comprising a second passage constructed and configured for the flow of a liquid substance; said system additionally including substance source means operatively connected to said second passage of said device.

11. The system of claim 9 additionally including means for sensing the temperature within said outer zone of said first chamber of said device, and for generating an electrical signal indicative thereof; and means responsive to such an electrical signal.

12. A method for promoting the transfer of a substance through a membranous layer at a treatment site, said method comprising:
(a) providing a device having wall structure by which is defined first and second, directly adjacent lateral chambers, said chambers having open outer ends disposed on a substantially common plane, and being otherwise isolated from one another;
(b) pressing said device against the membranous layer at the treatment site so as to cause the membranous layer to overlie and close said outer ends of said chambers;
(c) applying a treating substance to the treatment site, said steps (b) and (c) being so effected as to dispose said substance within a zone at said outer end of said first chamber of said device;
(d) subjecting said site and said substance thereon to ultrasonic vibrational energy;
(e) pressurizing said first chamber so as to subject said site and said substance thereon to positive pressure, during at least a portion of the time that said subjecting step (d) is carried out; and
(f) evacuating said second chamber so as to subject said site to negative pressure during at least part of said portion of time.

13. The method of claim 12 wherein said applying step additionally includes a step of supplying said treating substance through said device and within said outer end zone.

14. The method of claim 13 wherein said treatment substance is a liquid medicament.

15. The method of claim 12 wherein said first chamber of said device is positively pressurized by introducing a gaseous substance into said outer end zone.

16. The method of claim 12 wherein said second chamber of said device surrounds said first chamber thereof.

17. The method of claim 12 including the additional step of sensing the temperature within said outer end zone.

18. The method of claim 12 wherein a positive pressure of 10 to 80 $lb/in^2$ is applied in said step (e).

19. The method of claim 18 wherein a negative pressure of 10 to 30 $lb/in^2$ is drawn in said step (f).

* * * * *